(12) United States Patent
Reynolds et al.

(10) Patent No.: US 9,402,640 B2
(45) Date of Patent: Aug. 2, 2016

(54) ALIGNMENT GUIDE WITH EMBEDDED FEATURES FOR INTRA-OPERATIVE FLUORO-CHECKS

(71) Applicant: Wright Medical Technology, Inc., Arlington, TN (US)

(72) Inventors: David Reynolds, Lakeland, TN (US); Paul Stemniski, Arlington, TN (US); Sarah Lancianese, Orlando, FL (US); Richard Obert, Germantown, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 61 days.

(21) Appl. No.: 13/734,616

(22) Filed: Jan. 4, 2013

(65) Prior Publication Data
US 2014/0163570 A1    Jun. 12, 2014

Related U.S. Application Data

(60) Provisional application No. 61/736,302, filed on Dec. 12, 2012.

(51) Int. Cl.
*A61B 17/17* (2006.01)
*A61B 17/56* (2006.01)

(52) U.S. Cl.
CPC ..... *A61B 17/1703* (2013.01); *A61B 2017/1775* (2013.01); *A61B 2017/568* (2013.01)

(58) Field of Classification Search
CPC ........... A61B 17/1703; A61B 17/1717; A61B 2017/1775; A61B 17/15; A61B 17/17; A61B 17/1721; A61B 17/1725; A61B 17/175

USPC .......................................... 606/86 R, 87, 104
See application file for complete search history.

(56) References Cited

U.S. PATENT DOCUMENTS

| 3,727,611 | A | * | 4/1973 | Schultz ............................ 606/96 |
| 3,842,824 | A | * | 10/1974 | Neufeld ......................... 606/309 |
| 4,719,907 | A | * | 1/1988 | Banko et al. ..................... 606/96 |
| 5,768,134 | A |   | 6/1998 | Swaelens et al. |

(Continued)

FOREIGN PATENT DOCUMENTS

| GB | 2402883 A | 12/2004 |
| JP | 2009-148597 A | 7/2009 |

(Continued)

OTHER PUBLICATIONS

European Search Report for Application No. EP 13 19 6782 dated Feb. 26, 2014.

*Primary Examiner* — Matthew Lawson
*Assistant Examiner* — Amy Sipp
(74) *Attorney, Agent, or Firm* — Duane Morris LLP

(57) ABSTRACT

A surgical device having an assembly used to position a patient-specific surgical instrument with a bone of a patient, the assembly having radio-opaque and radiolucent portions that provide an indication of the instrument, and corresponding implant's alignment with respect to the bone, as well as an indication that the angle of the projection (or orientation of the view) of the alignment guide to assess the placement of the alignment guide relative to the underlying bony anatomy. The radio-opaque portion may include a plurality of Kirschner wires, fiducial markers, and may include a void allowing for alignment down a first length of the radio-opaque portion. Embodiments may be used with intra-operative fluoroscopy.

10 Claims, 8 Drawing Sheets

(56) References Cited

U.S. PATENT DOCUMENTS

| | | | |
|---|---|---|---|
| 6,712,856 B1* | 3/2004 | Carignan et al. | 623/20.35 |
| 7,534,246 B2 | 5/2009 | Reiley et al. | |
| 2005/0004676 A1* | 1/2005 | Schon et al. | 623/21.18 |
| 2006/0142870 A1* | 6/2006 | Robinson et al. | 623/21.18 |
| 2006/0212118 A1* | 9/2006 | Abernathie | 623/17.11 |
| 2006/0229730 A1* | 10/2006 | Railey et al. | 623/21.18 |
| 2007/0270851 A1* | 11/2007 | Erickson | A61B 17/7059 623/17.16 |
| 2008/0086137 A1* | 4/2008 | Probe | A61B 17/748 606/246 |
| 2008/0287954 A1* | 11/2008 | Kunz et al. | 606/87 |
| 2009/0182433 A1* | 7/2009 | Reiley et al. | 623/18.11 |
| 2010/0023065 A1* | 1/2010 | Welch et al. | 606/86 R |
| 2010/0318088 A1* | 12/2010 | Warne et al. | 606/87 |
| 2011/0218542 A1* | 9/2011 | Lian | 606/88 |
| 2012/0277745 A1* | 11/2012 | Lizee | 606/59 |

FOREIGN PATENT DOCUMENTS

| | | |
|---|---|---|
| WO | 2008/017501 A1 | 2/2008 |
| WO | 2008/124521 A1 | 10/2008 |
| WO | 2012/007054 A1 | 1/2012 |
| WO | 2012/107061 A1 | 8/2012 |

* cited by examiner

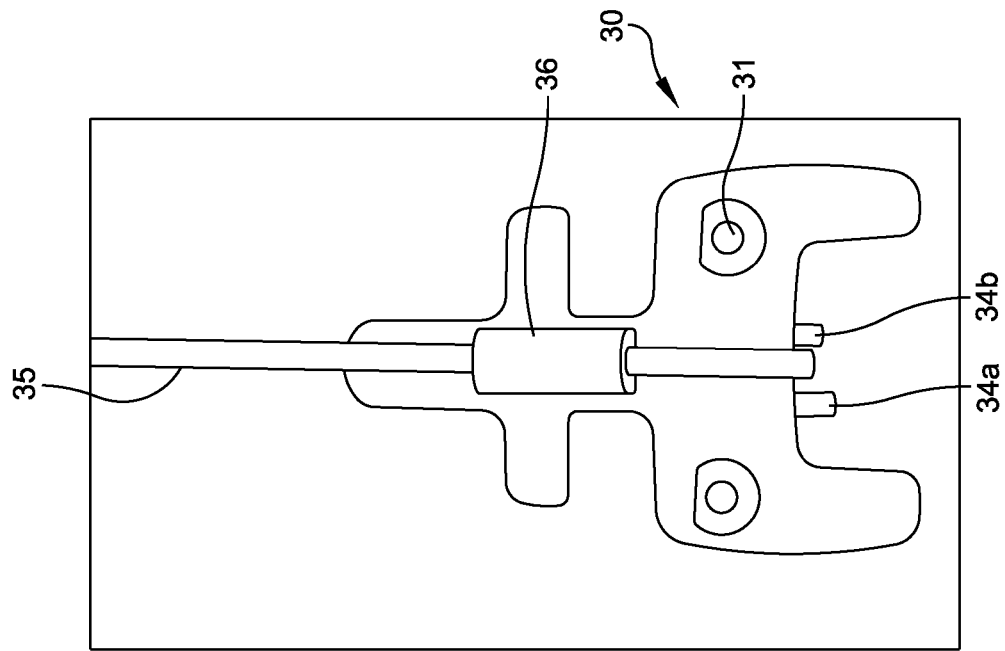
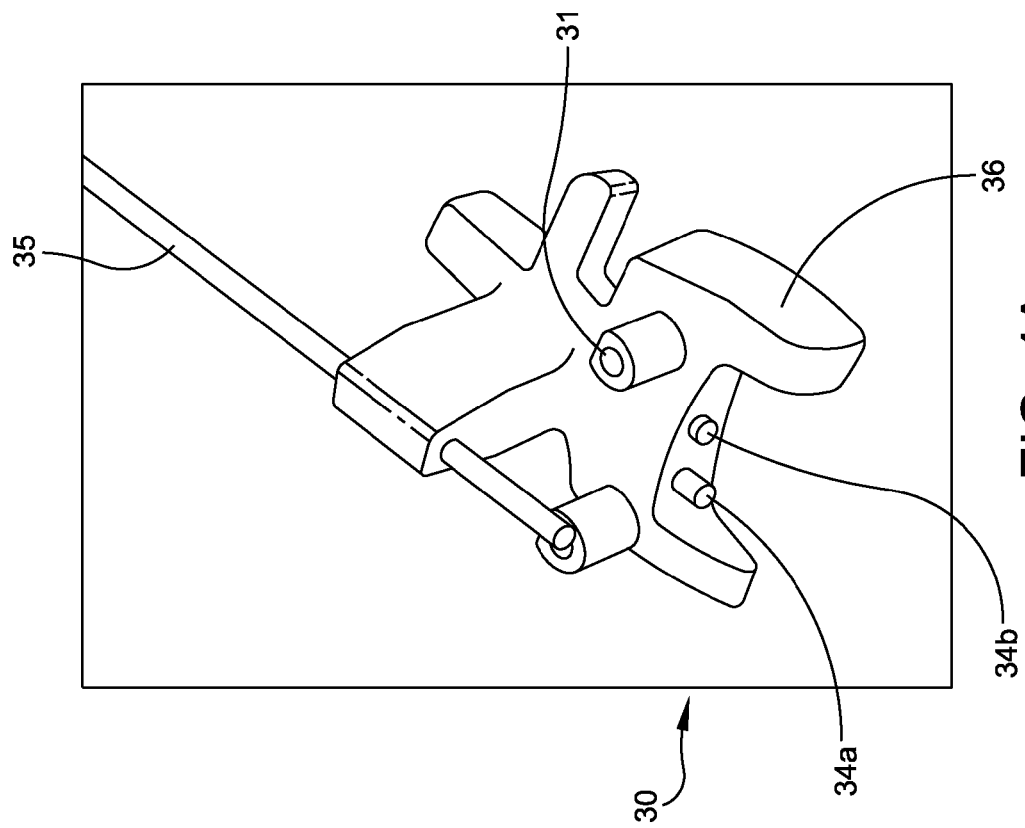

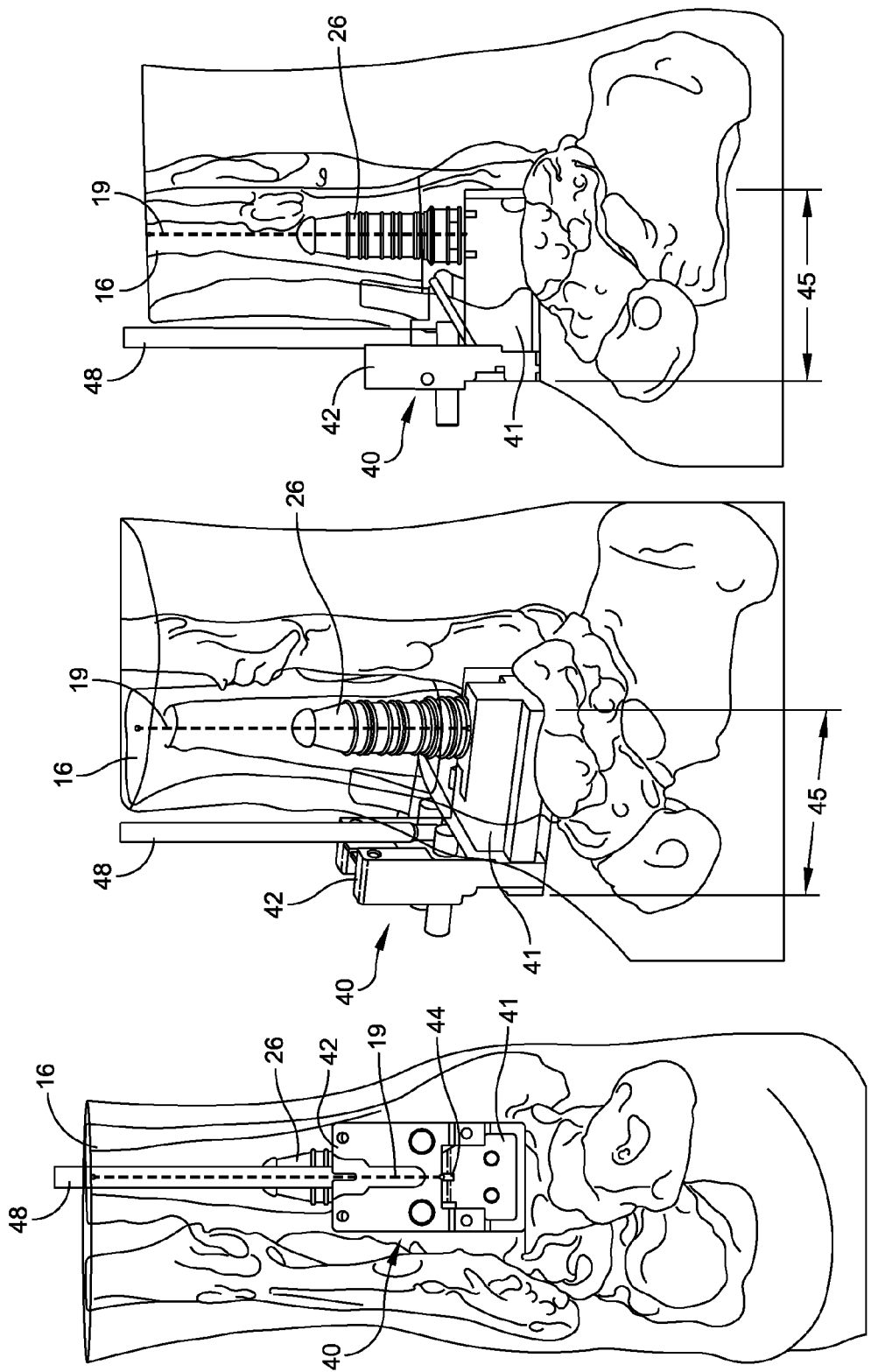

ALIGNMENT GUIDE WITH EMBEDDED FEATURES FOR INTRA-OPERATIVE FLUORO-CHECKS

RELATED APPLICATIONS

The present application is a non-provisional application of and claims the filing date priority benefit of provisional application No. 61/736,302 entitled "Alignment Guide with Embedded Features for Intra-Operative Fluoro-Checks" filed on Dec. 12, 2012, which is hereby incorporated by reference in its entirety.

FIELD OF DISCLOSURE

The disclosed system and method generally relate to surgical guides. More specifically, the disclosed system and method relate to surgical guides for orthopedic procedures.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint or not properly aligned, discomfort to the patient, gait problems, or degradation of the prosthesis may result.

Many surgical procedures employ the use of intra-operative fluoroscopy to check the alignment of the instrumentation relative to the patient's anatomy, such as the intramedullary cavities that are to be prepared to receive the joint replacement prosthesis; however, the use of intra-operative fluoroscopy may have drawbacks. One such drawback is that the use of fluoroscopy to check the alignment of intramedullary cavities formed during surgery may increase the overall length of the surgical procedure as time is taken to acquire and evaluate the fluoroscopic images. Long surgery times may lead to increased tourniquet time for the patient and may therefore increase recovery time.

Another drawback of fluoroscopy is exposing the patient and others in the operating room to the ionized radiation. For example, the U.S. Food and Drug Administration ("FDA") has issued several articles and public health advisories concerning the use of the fluoroscopy during surgical procedures. Consequently, even though steps are taken to protect the patient and other from the ionized radiation, it is virtually impossible to eliminate all risk associated with the ionized radiation.

Thus, it is desirable to overcome the limitations of the prior art and provide an efficient fluoroscopy check of the alignment of prostheses with or without the assistance of a preoperative plan or assessment.

Further, achieving a proper vantage point is important when assessing an internal anatomic feature with an external radio-opaque indicator. For example, if an object is not properly aligned with a respective imaging system, projection of the external radio-opaque indicator may provide an improper assessment. This is known as parallax. Parallax can also cause distortion of a projected image due to the non-parallel rays from the x-ray source. Therefore, establishing the proper view of the subject matter herein is key, and embodiments disclosed herein describe a feature to assist in obtaining such a proper view.

For patient-specific surgical alignment guides, surgical planning for implant sizing and alignment may be performed pre-operatively based on a computer tomography (CT), magnetic resonance imaging (MRI) or other three dimensional (3D) medical imaging dataset, usually in a 3D computer aided design (CAD) environment. Based on the planned location and alignment of the respective implants, the surgical alignment guide may be designed to replicate the planned implant alignment in concert with the other surgical preparation instruments by fitting over the patient's bone and/or cartilage in one specific position based on the topography of the patient's anatomy. As an additional intra-operative check a fluoro image may be useful in confirming that the location of the alignment guide has been achieved to the surgeon's satisfaction. Such an ability to check the alignment of the guide early in the surgical procedure, prior to fully committing to the placement of the alignment guide, may reduce the risk of improperly preparing the bone and give the surgeon an opportunity to find a location and alignment of the guide that meets his expectations.

SUMMARY

One embodiment of the present subject matter provides a patient-specific surgical device having an assembly to position a surgical implant or portion thereof with a bone of a patient, the assembly including radio-opaque and radiolucent portions. These radio-opaque and radiolucent portions may provide an indication of the placement and alignment of the instrument with respect to the bone. Exemplary radio-opaque portions may include a series of Kirschner wires, plural fiducial markers, and/or a radio-opaque portion having one or more voids allowing for alignment down a first length of the radio-opaque portion.

Another embodiment of the present subject matter provides a method of aligning a patient-specific alignment guide instrument. The method may include the steps of attaching an assembly to a surgical instrument or portion thereof, the assembly having radio-opaque and radiolucent portions and aligning the instrument with the bone by using the radio-opaque and radiolucent portions of the assembly. Exemplary radio-opaque portions may include a series of Kirschner wires, plural fiducial markers, and/or a radio-opaque portion having one or more voids allowing for alignment down a first length of the radio-opaque portion. One exemplary alignment step may include aligning the first and second Kirschner wires in the first plane with the third Kirschner wire in the second plane such that a projection of the third Kirschner wire onto the first plane along a normal axis to the first plane is between the first and second Kirschner wires. Another exemplary alignment step may include aligning the fiducial markers to form a cross hair. A further exemplary alignment step may include aligning a void down a first length of the radio-opaque portion, the first length being in line with a desired projection angle. Yet another exemplary alignment step may include using a pre-operative alignment report to assist in the alignment of the instrument with the bone.

These embodiments and many other objects and advantages thereof will be readily apparent to one skilled in the art to which the invention pertains from a perusal of the claims, the appended drawings, and the following detailed description of the embodiments.

BRIEF DESCRIPTION OF THE DRAWINGS

FIGS. 4A and 4B are a perspective view and a front plan view, respectively, of the alignment guide depicted in FIGS. 2 and 3.

FIG. 7B is a front plan view of a tibial implant with an alignment guide shown in FIG. 7A in an aligned position from the proper view orientation.

FIGS. 7C and 7D are a perspective view and a side plan view, respectively, of the alignment guide and resulting implant placement and alignment depicted in FIG. 7B.

DETAILED DESCRIPTION

Figure 1:
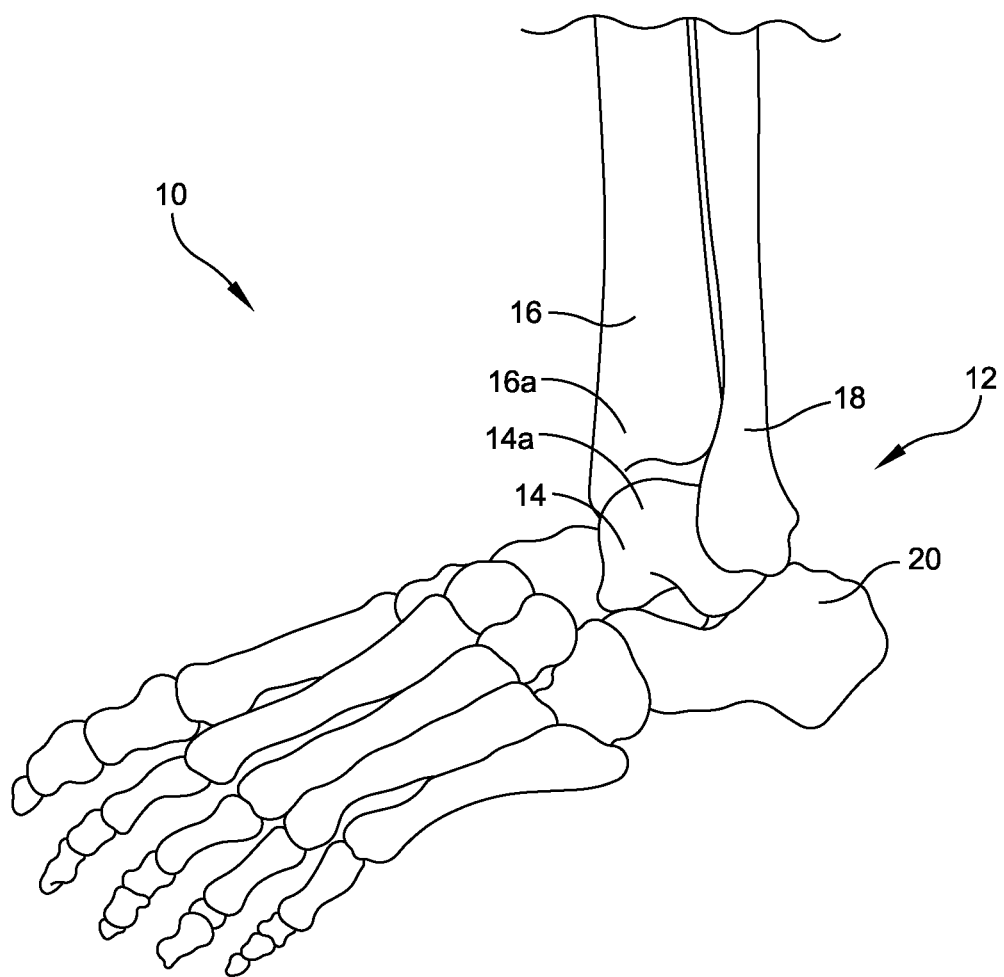
FIG. 1 is an illustration of the bones of a human foot and ankle.

With reference to the figures, where like elements have been given like numerical designations to facilitate an understanding of the present subject matter, the various embodiments of an alignment guide with embedded features for intra-operative fluoro-checks and method for aligning an implant are described.

It should be noted that the figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods may advantageously utilize custom manufactured surgical instruments, guides, and/or fixtures that are based upon a patient's anatomy to maximize the accuracy of assessing the alignment of the guide using fluoroscopy during a surgical procedure. These custom instruments, guides, and/or fixtures may be created by imaging a patient's anatomy with a computer tomography ("CT") scanner, a magnetic resonance imaging ("MRI") machine, or like medical imaging technology prior to surgery and utilizing these images to create patient-specific instruments, guides, and/or fixtures. This is generally termed as a preoperative assessment or plan and may be used in conjunction with intra-operative tools to accurately implement such a plan. Exemplary preoperative assessments or plans may allow a surgeon to specify the size, position and orientation of a patient's anatomical components and/or subsequent implant components within the joint or bone at issue based upon preoperative CT or MRI images. Of course, final component size and position may be determined intra-operatively through direct visualization by the surgeon with or without the aid of fluoroscopy.

Although the following description of the custom patient-specific instruments are described with respect to a foot 10 and ankle 12, one skilled in the art will understand that the systems and methods described herein may be utilized in connection with other joints and respective bones including, but not limited to, knees, hips, arms, shoulders, and the like. Thus, the claims appended herewith should not be limited to an ankle and the bones associated therewith. As shown in FIG. 1, a typical human foot 10 includes an ankle joint 12 formed between a talus 14, which is disposed on a calcaneus 20, and a tibia 16 and fibula 18.

A CT or MRI scanned image or series of images may be taken of a patient's ankle 12 (or other joint and respective bones) and then converted from, e.g., a DICOM image format, to a solid computer model of the ankle including the calcaneus, talus, tibia, navicular, and fibula to determine implant alignment, type, and sizing using specialized modeling methods that are often embodied in computer software. Computer generated solid models that are derived from the data of the CT or MRI scan image will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like. The methods disclosed in U.S. Pat. No. 5,768,134, issued to Swaelens et al., which is incorporated by reference herein in its entirety, have been found to yield adequate conversions of data of CT or MRI scan images to solid computer models. In some embodiments, images are made of a foot 10, i.e., the calcaneus 20, talus 14, tibia 16, and fibula 18 of a patient using a CT or MRI machine, or other digital image capturing and processing unit as is understood by one skilled in the art and a model generated.

Figure 3:
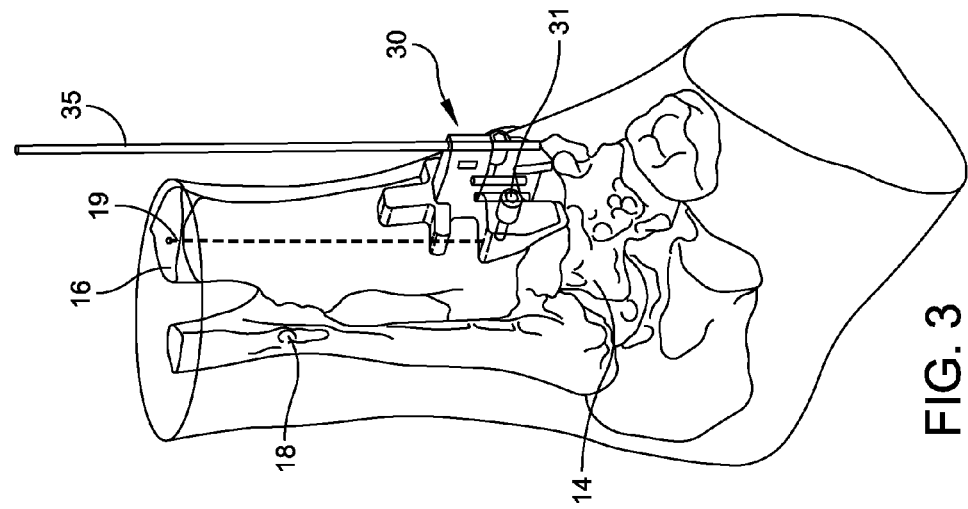
FIG. 3 is a front quadrant perspective view of a tibial alignment guide according to an embodiment of the present subject matter.
Figure 2:
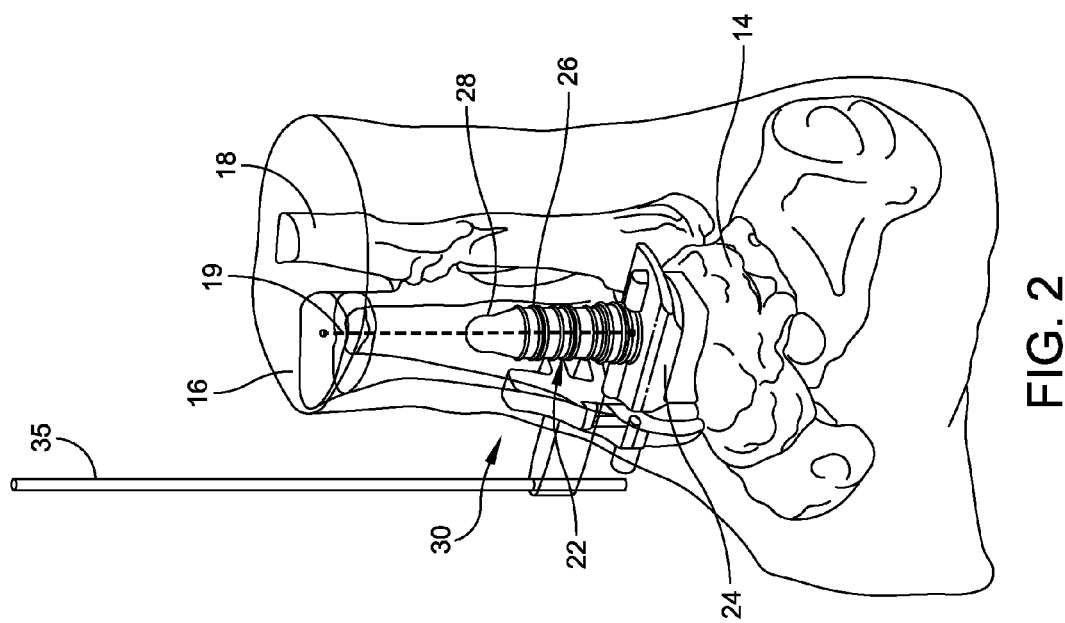
FIG. 2 is a rear-quadrant perspective view simultaneously showing a tibial implant in its planned location with an alignment guide according to an embodiment of the present subject matter.

FIG. 2 is a virtual, rear-quadrant perspective view simultaneously depicting a tibial implant or prosthesis in its pre-operatively determined position with an alignment guide according to an embodiment of the present subject matter. With regard to the term "virtual," it should be noted that implants would not be in the respective bone at the time an exemplary alignment guide was being used. Rather, a "virtual" view may be generated using computer aided design during pre-operative planning in which the respective implants may be placed and the alignment guide designed to achieve proper implant location. FIG. 3 is a front quadrant perspective view of a tibial alignment guide according to an embodiment of the present subject matter. With reference to FIGS. 2 and 3, an exemplary implant such as a tibial implant 22 may be inserted or implanted into a respective bone, e.g., a tibia 16, by conventional means including the removal of bone material from the tibia 16, fibula 18 and/or talus 14 using chisels, screws, drills, reamers and other conventional removal tools. The tibia 16, fibula 18 and/or talus 14 may then be sized, reshaped and/or resected to accept appropriate talar, tibial and/or fibular fixtures or implants. These fixtures may be mechanically affixed to the respective bone by screws, nails, bone cement and the like and may have surface-matched shapes specific to a patient's anatomy. One exemplary implant 22 may be, but is not limited to, a Wright Medical Technologies, Inc. INBONE® total ankle system described in U.S. Pat. No. 7,534,246 the entirety of which is incorporated herein by reference. The tibial implant 22 may include a laterally extending tray or base 24 shaped to conform to the patient's distal tibia after the distal portion of the tibia 16 has been appropriately shaped and resected. The tibial implant or prosthesis 22 may also include a stem or plug 26, sectioned or otherwise, extending generally perpendicular to a plane formed by the tibial base 24. The stem 26 may be placed in a surgically formed opening extending into a patient's intramedullary canal 28. A plastic, polymeric insert may also be attached to the tibial base 24 which provides a tibial articulating surface that articulates with the movement of the respective joint. A non-limiting, exemplary system and method for an ankle replacement is described in co-pending U.S. application Ser. No. 13/330,091 filed Dec. 19, 2011 and U.S. application Ser. No. 12/711,307, filed Feb. 24, 2010, the entirety of each being incorporated herein by reference.

FIGS. 4A and 4B are a perspective view and a front plan view, respectively, of the alignment guide depicted in FIGS. 2 and 3. With reference to FIGS. 2-4B, an exemplary patient-specific alignment guide 30 according to one embodiment of the present subject matter may be slidably attached or rigidly affixed to a portion of the patient's anatomy external or internal to the bone 16. For example, the alignment guide 30 may include one or more holes 31 which are adaptable to accept fixation pins (not shown), screws, or other features to affix the alignment guide 30 onto the bone. The pins or screws placed in the bone through the alignment guide may then be used to align bone preparation guides (cut guides, reamer holders, etc.) to properly prepare the bone for the implant 22 in a planned alignment. The alignment guide 30 may also be used by the surgeon, for example, to assess implant 22 component sizes and positions intra-operatively through direct visualization with or without the aid of fluoroscopy.

For example, the alignment guide 30 may include both radio-opaque 34a, 34b, 35 and radiolucent 36 portions, whereby the radio-opaque 34a, 34b, 35 and/or radiolucent portions 36 provide an indication of a portion of an implant with respect to the bony anatomy or a bone axis. Of course, the indication may represent the position or alignment of a portion of the implant with a longitudinal axis of the bone, the position of a portion of the implant with a transverse axis of the bone, the position of a portion of the implant with a resection plane of the bone, a drill location for the bone, a drill orientation for the bone, and/or the position of a portion of the implant with an axis of the implant stem. In one non-limiting embodiment, the radio-opaque portions 34a, 34b, 35 may include a plurality of Kirschner wires whereby two of the Kirschner wires 34a, 34b are located in a first plane and the third Kirschner wire 35 is located in a second plane, the first and second planes being parallel to each other and each Kirschner wire 34a, 34b, 35 being linearly parallel to the other Kirschner wires. In such an embodiment, the third Kirschner wire 35 may be adapted to be aligned with a longitudinal axis 19 of the bone or implant stem 26 (see FIGS. 2 and 3). Using an inter-operative fluoroscopic check, the surgeon may thus position or align the three Kirschner wires 34a, 34b, 35 to form a "gun sight" whereby the surgeon may align the first and second Kirschner wires 34a, 34b in the first plane with the third Kirschner wire 35 in the second plane such that a projection of the third Kirschner wire 35 onto the first plane along a normal axis to the first plane is between the first and second Kirschner wires 34a, 34b. This formation of a "gun sight" would generally indicate the proper view of the alignment guide has been attained (whether by fluoroscopy or by eye). Subsequent to identifying the proper view of the guide has been achieved, the long radio-opaque feature of the guide would allow for assessment of the position and alignment of the alignment guide relative to the bony anatomy. This long radio-opaque feature would correspond to some aspect (centerline, resection level, implant profile, size indicator, etc.) of the what would be the resulting position and alignment of the final implant 22, e.g., tibial tray or base 24 and stem 19. Such a positioning is exemplary only and should not limit the scope of the claims appended herewith as the formation of such an aligned gun sight may also represent a proper positioning or alignment of a portion of the implant with a longitudinal axis of the bone, a portion of the implant with a transverse axis of the bone, a portion of the implant with a resection plane of the bone, a drill location for the bone, and/or a drill orientation for the bone.

Figure 5B:
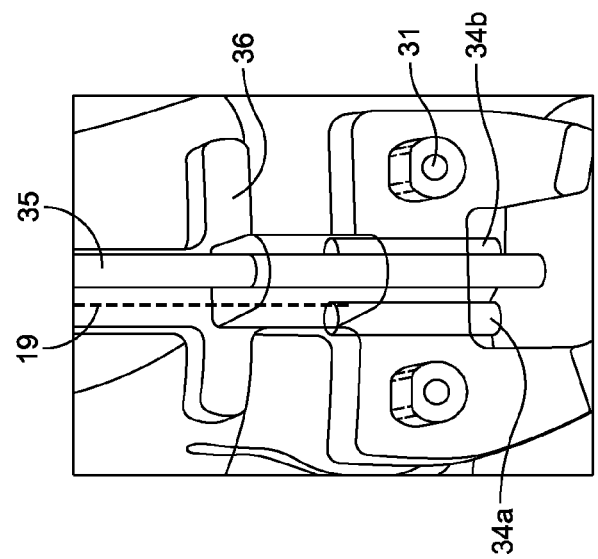
FIG. 5B is a detailed view of the alignment guide of FIG. 5A.
Figure 5A:
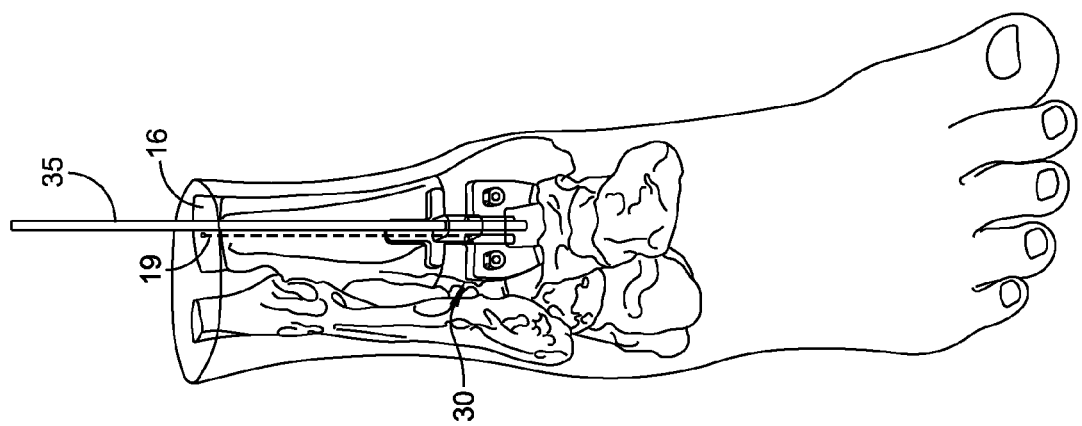
FIG. 5A is a front plan view of a tibial alignment guide in the proper position but viewed from an improper perspective being that it is being viewed from a slightly external orientation from the true AP view.
Figure 6A:
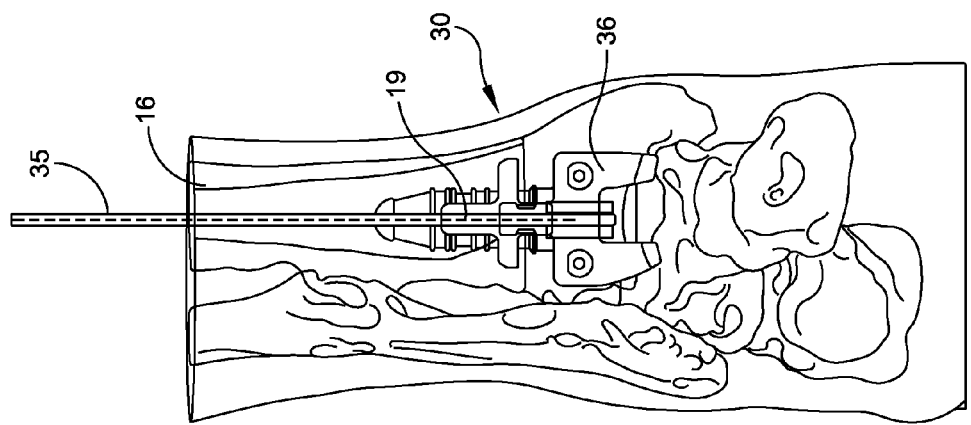
FIG. 6A is a front plan view simultaneously showing what the tibial implant alignment will be and the alignment guide of FIGS. 4A-4B in a properly aligned position from a properly aligned view.
Figure 6B:
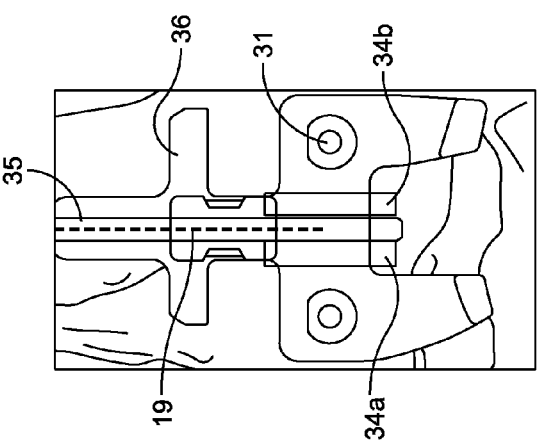
FIG. 6B is a detailed view of the alignment guide of FIG. 6A.

FIG. 5A is an imperfect (oblique) anterior view of the alignment guide of FIGS. 4A-4B in a non-aligned position, and FIG. 5B is an exploded view of the alignment guide of FIG. 5A. With reference to FIGS. 5A and 5B, through use of fluoroscopy, a surgeon may determine that the base 24 or other section of the tibial implant 22 is misaligned with the implant stem axis 19 or bone axis as shown by the misalignment of two of the Kirschner wires 34a, 34b located in a first plane with the third Kirschner wire 35 located in a second plane. Such a misalignment of these Kirschner wires results in the lack of formation of an aligned gun sight of the wires. Conversely, FIG. 6A is a virtual front view of what will be the resulting placement and alignment of a tibial implant with the alignment guide of FIGS. 4A-4B from the proper vantage point, and FIG. 6B is an exploded view of the alignment guide of FIG. 6A. With reference to FIGS. 6A and 6B, through use of fluoroscopy, a view from the proper vantage point is identified by the formation of an aligned gun sight. Establishing a proper view orientation eliminates the effect of parallax and provides a surgeon with the proper view to assess the placement and alignment of the patient-specific alignment guide. For example, a surgeon may use the third Kirschner wire 35 to assess the placement of the guide relative to an intended feature of the patient's anatomy such as, but not limited to, the intramedullary canal or bone axis 19 or other anatomic reference identifiable on fluoroscopic radiography intraoperatively. An alignment of these Kirschner wires results in the formation of an aligned gun sight of the wires and thus intraoperatively illustrates what will be the alignment of the base 24 or stem 26 or other section of the tibial implant 22 with the implant stem axis 19 and/or bone axis. Of course, the formation of such an aligned gun sight may also represent a proper positioning or alignment of a portion of the implant with a longitudinal axis of the bone, a portion of the implant with a transverse axis of the bone, a portion of the implant with a resection plane of the bone, a drill location for the bone, and/or a drill orientation for the bone.

Figure 7A:
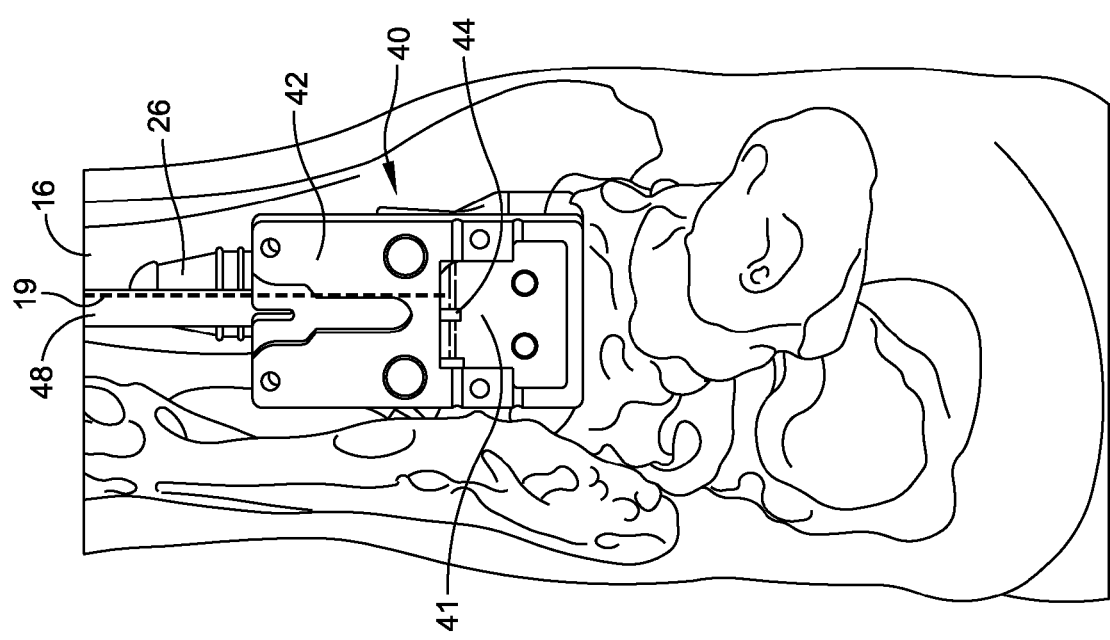
FIG. 7A is a front plan view simultaneously showing the planned tibial implant placement and alignment and an alignment guide according to another embodiment of the present subject matter viewed from an improper perspective being that it is being viewed from a slightly internal orientation from the true AP view.

FIG. 7A is a virtual front plan view of a tibial implant with an alignment guide according to another embodiment of the present subject matter from an improper vantage point. FIG. 7B is a virtual front plan view of an alignment guide shown in FIG. 7A when viewed from the appropriate vantage point. FIGS. 7C and 7D are a virtual perspective view and a side plan view, respectively, of FIG. 7B. With reference to FIGS. 7A-7D, another exemplary alignment guide 40 may include both radio-opaque 41 and radiolucent 42 portions, whereby the radio-opaque 41 and/or radiolucent portions 42, 48 provide an alignment indication of the alignment guide 40 which is used to represent what will be the resulting alignment of a portion of an implant with respect to a bone axis, implant axis 19, resection plane, or other feature. In this depicted embodiment, the radio-opaque portion 41 may be comprised of a metal or other radio-opaque material and may include a void 44 allowing for alignment down a lateral length 45 of the radio-opaque portion. This lateral length 45 may generally be on a plane perpendicular to a longitudinal axis 19 of the bone or implant stem 26 when the portion of the alignment guide which represents when the implant will be properly aligned with the axis 19. The embodiment depicted in FIGS. 7A-7D is also illustrated using an extra-medullary alignment rod 48; however, it is envisioned that exemplary embodiments of the present subject matter may be employed without such a rod 48. In the depiction in FIG. 7B, through use of fluoroscopy, a surgeon may assess what the resulting implant base 24 or tibial implant 22 alignment will be if they were to proceed with the subsequent instrumentation that will prepare the bone for the implant, based on the alignment and position the guide is conveying. If the surgeon determines he is dissatisfied with what will the resulting alignment would be, an intraoperative adjustment can be made to suit his judgment. If an observable void (FIG. 7A) 44 within the guide 40 is lacking, this would indicate that a proper view of the guide has not been achieved, thus making assessment relative to the bone meaningless.

Figure 8C:
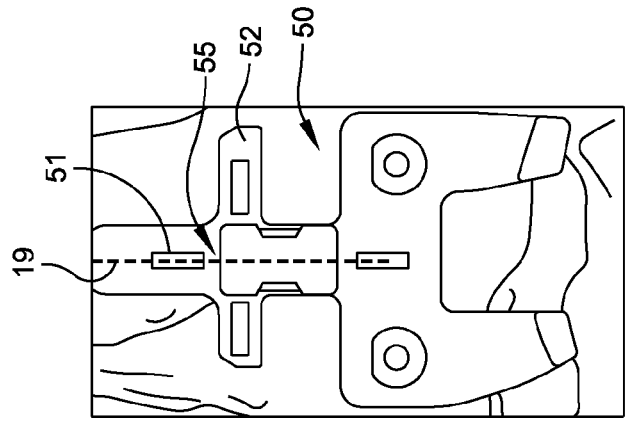
FIG. 8C is a detailed view of FIG. 8B.
Figure 8B:
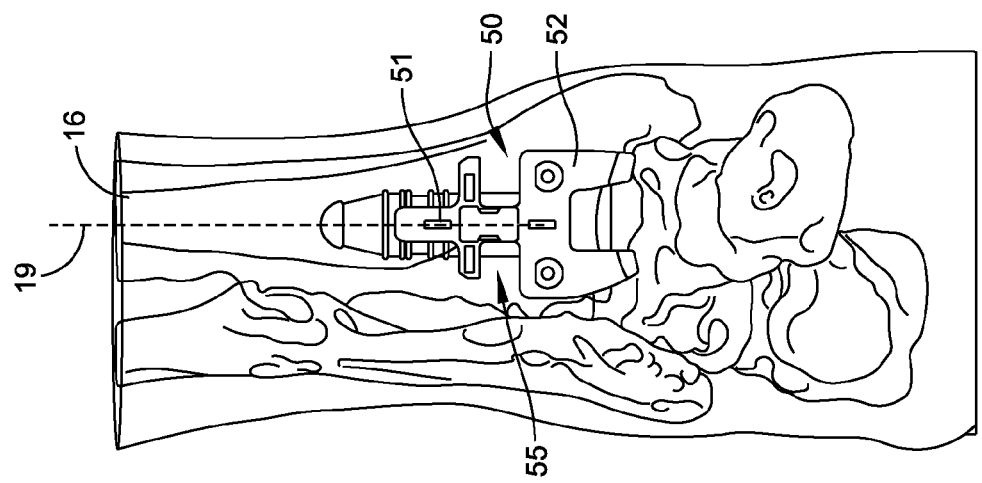
FIG. 8B is a rear plan view of a tibial implant with the alignment guide shown in FIG. 8A in an aligned position.
Figure 8A:
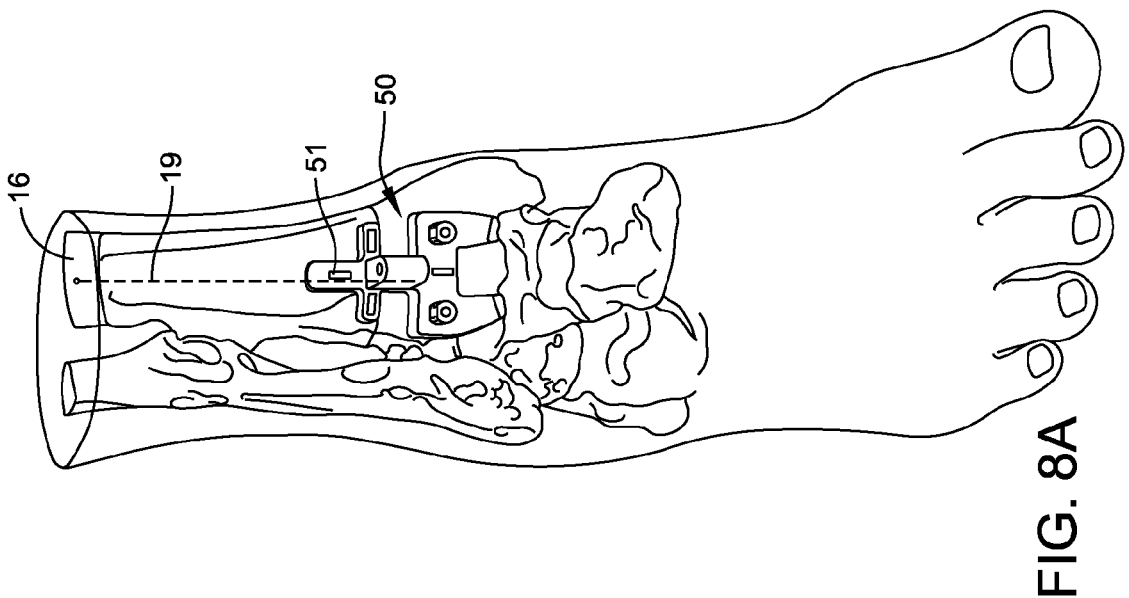
FIG. 8A is a front plan view of a tibial alignment guide according to a further embodiment of the present subject matter in a non-aligned position.

FIG. 8A is a front view of a tibial implant with an alignment guide according to a further embodiment of the present subject matter in an improperly aligned view. FIG. 8B is a front plan view of a tibial implant with an alignment guide shown in FIG. 8A in an aligned position, and FIG. 8C is a detailed view of FIG. 8B. With reference to FIGS. 8A-8C, a further exemplary alignment guide 50 may include both radio-opaque 51 and radiolucent 52 portions, whereby the radio-opaque 51 and/or radiolucent portions 52 provide an alignment indication of a portion of an implant with respect to a bone axis or implant axis 19. In this embodiment, the radio-opaque portion 51 may be comprised of a plurality of fiducial markers (e.g., two, three, four or more markers). One or more of these fiducial markers may be provided out-of-plane to indicate that an appropriate vantage point has been achieved. Exemplary fiducial markers may be pins, rods, spheres or other common fiducial markers employed in the industry. In the depiction in FIG. 8A, through use of fluoroscopy, a surgeon would be able to determine that the base 24 or other section of the tibial implant 22 is aligned or misaligned with the implant stem axis 19, bone axis or other feature as shown by lack of the formation of a properly aligned cross hair. Thus, this lack of a formed cross hair may generally indicate a misalignment of a section of the tibial implant 22, e.g., tibial tray or base 24, with the implant stem axis 19, bone axis or other feature. By way of further example, if radio-opaque 51 and radiolucent 52 portions were lined up with similar fiducials more anterior or posterior to these portions 51, 52, then a proper cross hair may be formed through such items positioned in differing planes. It follows that such fiducial markers may be employed in any of the embodiments described herein to assist a surgeon in alignment of instrumentation relative to a respective patient's anatomy. In the depiction in FIGS. 8B-8C, through use of fluoroscopy, a surgeon may determine that the base 24 or other section of the tibial implant 22 is properly aligned with the implant stem axis 19 or bone axis as shown by the formation of a cross hair 55 by the plural fiducial markers. Such a formation of the cross hair 55 in the guide 40 may generally indicate a proper alignment of a section of the tibial implant 22, e.g., tibial tray or base 24, with the implant stem axis 19 or bone axis. Of course, such a depiction is exemplary only and should not limit the scope of the claims appended herewith as the formation of such an aligned cross hair may also represent a proper positioning or alignment of a portion of the implant with a longitudinal axis of the bone, a portion of the implant with a transverse axis of the bone, a portion of the implant with a resection plane of the bone, a drill location for the bone, and/or a drill orientation for the bone.

Although the views referenced and depicted are generally shown in the coronal plane, one skilled in the art will understand that embodiments of the present subject matter may be implemented for other view orientations including lateral, transverse, and any other oblique views.

Although reference has been made to a patient's talus, tibia, fibula, and ankle joint, one skilled in the art will understand that embodiments of the present subject matter may be implemented for other respective bones including, but not limited to, bones at the knee, hip, shoulder, or other joints, as well as for patient-specific alignment guides for spinal surgery, and craniofacial reconstruction. Thus, the disclosed devices and methods may advantageously utilize custom manufactured surgical instruments, guides, and/or fixtures that are based upon a patient's anatomy to reduce the use of fluoroscopy during a surgical procedure for a multitude of joints and bones.

It may be emphasized that the above-described embodiments, particularly any "preferred" embodiments, are merely possible examples of implementations and merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

While this specification contains many specifics, these should not be construed as limitations on the scope of the claimed subject matter, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

As shown by the various configurations and embodiments illustrated in FIGS. 1-8C, an alignment guide with embedded features for intra-operative fluoro-checks and method for aligning an implant have been described.

While preferred embodiments of the present subject matter have been described, it is to be understood that the embodiments described are illustrative only and that the scope of the invention is to be defined solely by the appended claims when accorded a full range of equivalence, many variations and modifications naturally occurring to those of skill in the art from a perusal hereof.

What is claimed is:

1. A surgical alignment device comprising:
    a first radio-opaque portion located in a first plane and supported by a first radiolucent portion;
    a pair of radio-opaque portions located in a second plane that is parallel to the first plane, each of the pair of radio-opaque portions being linearly parallel to each other and to the first radio-opaque portion, wherein the first radio-opaque portion and the pair of radio-opaque portions are in the form of Kirschner wires;
    a second radiolucent portion defining a pair of spaced apart holes each defining a respective axis that is perpendicular to a length of the first radio-opaque portion; and
    a portion having a surface-matched topography that conforms to a patient's bony or cartilaginous anatomy upon which the device is to be positioned,
    wherein the first radio-opaque portion is adapted to be aligned with a longitudinal axis of a bone of the patient.

2. The surgical alignment device of claim 1 wherein the Kirschner wires are adaptable to form a gun sight.

3. The surgical alignment device of claim 1 wherein, when the first radio-opaque portion is aligned with the longitudinal axis of the bone, an indication is provided that represents an alignment of a portion of an implant with the longitudinal axis of the bone, an alignment of a portion of the implant with a transverse axis of the bone, a resection plane, a drill location, a drill orientation, or an axis of the implant.

4. The surgical alignment device of claim 1 wherein at least one of the first radiolucent portion and the second radiolucent portion is comprised of radiolucent nylon.

5. The surgical alignment device of claim 1, wherein the first bone is a tibia.

6. A method comprising the steps of:
    placing a surgical alignment guide on a bone or cartilaginous surface of a patient, the surgical alignment guide comprising
        a first radio-opaque portion located in a first plane and supported by a first radiolucent portion,
        a pair of radio-opaque portions located in a second plane that is parallel to the first plane, each of the pair of radio-opaque portions being linearly parallel to each other and to the first radio-opaque portion, wherein the first radio-opaque portion and the pair of radio-opaque portions are in the form of Kirschner wires and
        a second radiolucent portion defining a pair of spaced apart holes each defining a respective axis that is perpendicular to a length of the first one of the radio-opaque portions; and
    aligning the first radio-opaque portion of the surgical alignment guide with a longitudinal axis of the bone of the patient by mating a portion of the surgical alignment guide having a surface-matched topography to the bone or cartilaginous surface of the patient.

7. The method of claim 6 wherein the step of aligning further comprises aligning the pair of radio-opaque portions in the first plane with the first radio-opaque portion in the second plane such that a projection of the first radio-opaque portion onto the first plane along a normal axis to the first plane is between the pair of radio-opaque portions.

8. The method of claim 6 wherein the step of aligning provides an indication representing an alignment of a portion of an implant with the longitudinal axis of the bone, an alignment of a portion of the implant with a transverse axis of the bone, a resection plane, a drill location, a drill orientation, or an axis of the implant.

9. The method of claim 6 wherein the step of aligning further comprises:
    using a pre-operative alignment report to assist in the alignment of an implant with the bone.

10. The method of claim 9 wherein the pre-operative alignment report includes computed tomography (CT) or magnetic resonance imaging (MRI) scan derived anatomy.

\* \* \* \* \*